(12) United States Patent
Millis et al.

(10) Patent No.: US 11,103,450 B2
(45) Date of Patent: Aug. 31, 2021

(54) POLYFUNCTIONAL RADICAL SCAVENGER HYDROGEL FORMULATION

(71) Applicant: RXOS Medical Inc., West Allis, WI (US)

(72) Inventors: Richard M. Millis, La Plata, MD (US); Jeffrey A. Niezgoda, West Allis, WI (US); Rajagopalan Sridhar, Brandywine, MD (US)

(73) Assignee: RXOS Medical Inc., West Allis, WI (US)

( * ) Notice: Subject to any disclaimer, the term of this patent is extended or adjusted under 35 U.S.C. 154(b) by 0 days.

(21) Appl. No.: 16/867,319

(22) Filed: May 5, 2020

(65) Prior Publication Data

US 2020/0261360 A1     Aug. 20, 2020

Related U.S. Application Data

(63) Continuation of application No. 14/588,811, filed on Jan. 2, 2015, now Pat. No. 10,660,851.

(51) Int. Cl.

| | | |
|---|---|---|
| *A61K 9/06* | (2006.01) | |
| *A61K 45/06* | (2006.01) | |
| *A61K 31/15* | (2006.01) | |
| *A61K 31/13* | (2006.01) | |
| *A61K 9/00* | (2006.01) | |
| *A61L 15/44* | (2006.01) | |
| *A61L 15/60* | (2006.01) | |
| *A61L 15/32* | (2006.01) | |
| *A61K 47/32* | (2006.01) | |
| *A61K 33/38* | (2006.01) | |
| *A61K 31/216* | (2006.01) | |
| *A61K 31/445* | (2006.01) | |

(52) U.S. Cl.
CPC .............. *A61K 9/06* (2013.01); *A61K 9/0014* (2013.01); *A61K 31/13* (2013.01); *A61K 31/15* (2013.01); *A61K 31/216* (2013.01); *A61K 31/445* (2013.01); *A61K 33/38* (2013.01); *A61K 45/06* (2013.01); *A61K 47/32* (2013.01); *A61L 15/325* (2013.01); *A61L 15/44* (2013.01); *A61L 15/60* (2013.01)

(58) Field of Classification Search
CPC .... A61K 47/32; A61K 31/216; A61K 31/445; A61K 31/13; A61K 31/15; A61K 45/06; A61K 9/06; A61K 9/00; A61K 33/38; A61L 15/32; A61L 15/44; A61L 15/60
See application file for complete search history.

(56) References Cited

U.S. PATENT DOCUMENTS

| | | |
|---|---|---|
| 3,644,363 A | 2/1972 | Kim |
| 4,898,901 A | 2/1990 | Ravichandran et al. |
| 5,219,710 A | 6/1993 | Horn et al. |
| RE35,112 E | 12/1995 | Carney et al. |
| 5,622,994 A | 4/1997 | Carney et al. |
| 5,679,691 A | 10/1997 | Ribier et al. |
| 5,962,469 A | 10/1999 | Thomas et al. |
| 6,455,589 B1 | 9/2002 | Ames et al. |
| 6,512,143 B1 | 1/2003 | Blixt |
| 6,610,284 B1 | 8/2003 | Labsky et al. |
| 7,429,545 B2 | 9/2008 | Lupia et al. |
| 7,537,754 B2 | 5/2009 | Devore et al. |
| 7,629,375 B2 | 12/2009 | Wang et al. |
| 8,173,843 B2 | 5/2012 | Durand et al. |
| 8,722,836 B2 | 5/2014 | Knott et al. |
| 8,778,969 B2 | 7/2014 | Proctor |
| 2003/0181527 A1 | 9/2003 | Anderson et al. |
| 2004/0102420 A1 | 5/2004 | Ames et al. |
| 2005/0096360 A1 | 5/2005 | Salter-Cid et al. |
| 2005/0182060 A1 | 8/2005 | Kelly et al. |
| 2005/0256088 A1 | 11/2005 | Ames |
| 2008/0280890 A1 | 11/2008 | Patil |
| 2009/0227572 A1 | 9/2009 | Barber et al. |
| 2010/0272790 A1 | 10/2010 | Morariu |
| 2011/0034485 A1 | 2/2011 | Wang et al. |
| 2012/0172452 A1 | 7/2012 | Perricone |
| 2014/0378444 A1 | 12/2014 | Wipf et al. |

FOREIGN PATENT DOCUMENTS

EP          1739098 A2      3/2007

OTHER PUBLICATIONS

Liu et al., "Delaying Brain Mitochondrial Decay and Aging with Mitochondrial Antioxidants and Metabolites", Ann. N.Y. Acad. Sci. 959: 133-166 (2002).
Pluronic, Basf, screen capture of https://worldaccount.basf.com/wa/NAFTA/Catalog/ChemicalsNAFTA/pi/BASF/Brand/pluronic, accessed May 12, 2017.
Kotamraju et al., "Doxorubicin-induced Apoptosis in Endothelial Cells and Cardiomyocytes is Ameliorated by Nitrone Spin Traps and Ebselen", Journal of Biological Chemistry, 275: 33585-33592 (2000).
Floyd et al., "Nitrones, their value as therapeutics and probes to understand aging", Mechanisms of Aging and Development, 123: 1021-1031 (2002).
Proctor et al., "SAINT-I Worked, But the Neuroprotectant is Not NXY-059", Stroke, 38: e109 (2007).
Nootropics (2007), accessed at http://nootropics.livejournal.com/14344.html, on May 12, 2017 pp. 1-3.
Australian Government, Examination report No. 1 for standard patent application, dated Sep. 12, 2018, 7 pages.
Diane E. Handy et al., "Redox Regulation of Mitochondrial Function", Antioxidants & Redox Signaling, Nov. 11, 2012, vol. 16, No. 11, pp. 1323-1367.

(Continued)

*Primary Examiner* — Zohreh A Fay
(74) *Attorney, Agent, or Firm* — Nyemaster Goode, P.C.

(57) ABSTRACT

A polyfunctional radical scavenger hydrogel formulation providing extended protection of the extracellular space within a wound site. The polyfunctional radical scavenger hydrogel formulation is generally formed from a hydrogel, a first radical scavenger and a second radical scavenger differing from the first radical scavenger with respect to at least one property. A portion of the first radical scavenger included with the formation and/or second radical scavenger included within the formulation may be dissolved, suspended and/or bonded to a polymer of the hydrogel.

18 Claims, No Drawings

(56) References Cited

OTHER PUBLICATIONS

Manish Mittal et al., "Reactive Oxygen Species in Inflammation and Tissue Injury", Antioxidants & Redox Signaling, Nov. 7, 2014, vol. 20, No. 7, pp. 1126-1167.

Asako Watanabe et al., "Production of Hydrogen Peroxide by Neutrophilic Polymorphonuclear Leukocytes in Patients With Diabetic Nephropathy", Journal of Clinical Laboratory Analysis, vol. 7: pp. 209-213, 1993.

Kye-Taek Lim et al., "Neuronal Cytotxicity of Oxygen Radical in Newborn Mouse Forebrain Culture", Korean Journal of Toxicology, 1995, vol. 11, No. 2, pp. 187-192.

Tory M. Hagen et al., "Mitochondrial Decay in Aging, Reversal through Supplementation of Acetyl-l-Carnitine and N-tert-Butyl-a-phenyl-nitronea", Annals of the New York Academy of Sciences, Nov. 20, 1998, vol. 854, pp. 214-223, Berkeley.

Hani Atamna et al., "N-t-Butyl Hydroxylamine, a Hydrolysis Product of a-Phenyl-N-t-butyl Nitrone, Is More Potent in Delaying Senescence in Human Lung Fibroblasts", The Journal of Biological Chemistry, Mar. 10, 2000, pp. 6741-6748, vol. 275, No. 10, The American Society for Biochemistry and Molecular Biology, Inc. USA.

Qin Chen et al., "Oxidative DNA Damage and senescence of human diploid fibroblast cells", Proceedings of the National Academy of Sciences of the United States of America, Cell Biology, May 1995, pp. 4337-4341, vol. 92, USA.

Taka'aki Ohkuma et al., "Some Physiochemical Properties of 2-Methyl-2-nitrosopropane, Phenyl-N-tert-Burtyl Nitrone, 5,5-Dimethylpyrroline-N-oxide, and 2,5,5-Trimethyl-pyrroline-N-oxide and the Feasibility of Their Use as Spin Traps in Aqueous Solution", Chemical and Pharmaceutical Bulletin, 1981, pp. 25-28, vol. 29, No. 1, The Pharmaceutical Society of Japan.

Kenneth Hensley et al., "Interaction of a-Phenyl-N-tert-Butyl Nitrone and Alternative Electron Acceptors with Complex I Indicates a Substrate Reduction Site Upstream from the Rotenone Binding Site", Journal of Neurochemistry, 1998, pp. 2549-2557, vol. 71, No. 6, Lippincott—Raven Publishers, Philadelphia, USA.

W.H. Munyon et al., "The Relation Between Glucose Utilization, Lactic Acid Production and Utilization and the Growth Cycle of L Strain Fibroblasts", Experimental Cell Research, 1959, pp. 490-498, vol. 17, Elsevier.

Stephen J. Weiss et al., "Role of Hydrogen Peroxide in Neutrophil-mediated Destruction of Cultured Endothelial Cells," The Journal of Clinical Investigation, Sep. 1981, pp. 714-721, vol. 68, The American Society for Clinical Investigation, Inc.

Edward G. Janzen et al., "On spin trapping hydroxyl and hydroperoxyl radicals", Canadian Journal of Chemistry, 1978, pp. 2237-2242, vol. 56, NRC Research Press.

K. Pal et al., Polymer Hydrogels: Characterization and Biomedical Applications—A mini review, Designed Monomers and Polymers 12 (2009), pp. 197-220.

Polysciences, Inc., New! Hydrophilic PEG Monomers and Marcomononers, PolyFacts, Monomers & Polymers, vol. 7, No. 2.

Floyd et al., Nitrones, their values as therapeutics and probes to understand aging, Mechanisms of Ageing and Development, 123, (2002), pp. 1021-1031.

Kao et al., Interaction of PMN-Derived Reactive Oxygen Species with Tetramethyl Piperidiene/2-Hydroxyethyl Methyl Methacrylate Superoxide Dismutase Mimetic.

Gua and Dipetro, Factors Affecting Would Healing, Journal of Dental Research 89(3), pp. 219-229, 2010.

Written Opinion dated Mar. 11, 2016, by the USPTO acting as the ISA in regards to Application No. PCT/US2015/068135.

POLYFUNCTIONAL RADICAL SCAVENGER HYDROGEL FORMULATION

CROSS-REFERENCE TO RELATED APPLICATIONS

This application claims priority to U.S. patent application Ser. No. 14/588,811, filed on Jan. 2, 2015, entitled "POLYFUNCTIONAL RADICAL SCAVENGER HYDROGEL FORMULATION," now U.S. Pat. No. 10,660,851, the disclosure of which is hereby incorporated herein by reference in its entirety.

BACKGROUND OF THE INVENTION

Field of the Invention

A polyfunctional radical scavenger hydrogel formulation providing extended protection of the extracellular space capable of assisting wounded tissue in transitioning from the inflammation phase to the proliferation phase of wound healing.

Description of Related Art

Wound healing is an ordered process consisting of four coordinated phases. In the first phase, hemostasis, fibroblasts and platelets are recruited to the site of injury to control bleeding through the formation of a clot. The clot releases various cytokines and growth factors, thereby sending signals to other cells to facilitate healing as they are programmed to do. For example, cytokines released from the clot recruit leukocytes, cells of the immune system, to the wound that initiate the next phase of wound healing, inflammation.

Inflammation is the second phase of healing. It is considered by many to be the most unpleasant, as it is associated with many negative responses. For instance, inflammation is marked by swelling, redness, irritation, throbbing pain and itchiness. Despite its unpleasant perception, inflammation is very important for proper wound healing as it is during this phase that the wound is cleared of devitalized and/or necrotic tissue, foreign debris and infectious organisms. In addition to protecting and cleaning the wound, inflammation also makes the wound ready to be repaired.

After being made ready for repair by the inflammation phase, wound healing enters the third phase, proliferation. It is during this phase that the collagen extracellular matrix, which acts as a scaffolding to support new cells, is laid. New cells produced during the proliferation phase utilize the extracellular matrix scaffolding to migrate into the wound. Eventually a sufficient amount of newly-formed connective tissue and blood vessels, known as granulation tissue, migrates across the collagen rich extracellular matrix to cover the wound. This migration of granulation tissue into the wound allows for the migration of new epithelial cells into the wound to replace lost tissue.

The wound then enters the remodeling phase during which time newly created tissue is slowly increased in strength and transformed into mature tissue.

While the phases of wound healing are designed to progress in an ordered cycle, with each phase instigating the next via the release of cytokines and growth factors, wounds can become stalled in, or regress backwards to, the inflammation phase. This is quite problematic as the inflammation phase is quite destructive. As mentioned above, the inflammation phase makes the wound ready for repair by cleaning the wound of debris and infectious organisms. A key cleaning agent utilized by neutrophil and macrophage leukocytes during the inflammation phase is reactive oxygen species.

Reactive oxygen species are very reactive oxygen containing molecules, including superoxide radicals and hydroxyl radicals. Neutrophils, an initial player in the inflammation phase, release reactive oxygen species to kill infectious organisms and breakdown debris. The reactive oxygen species released by neutrophils, however, are not smart bombs. Rather, reactive oxygen species indiscriminately damage whatever they come across. Consequently, reactive oxygen species fired off by neutrophils destroy infectious organisms and debris along with healthy cells.

Another function of the reactive oxygen species released by neutrophils is to signal macrophages to enter the wound site. Macrophages, as with neutrophils, utilize reactive oxygen species to kill infectious organisms. Generally, they do so by engulfing an infectious organism, and then once inside the macrophage, attacking it with internal stores of reactive oxygen species. If macrophages receive a sufficient signal from neutrophils, they release reactive oxygen species in a carpet bombing oxidative burst.

The release of indiscriminately destructive reactive oxygen species generally is more beneficial than harmful. However, if wound healing becomes stalled during the inflammation phase, or regresses backwards to the inflammation phase, the harm caused by the reactive oxygen species bombardment of the wound site may quickly outweigh the good. For example, the reactive oxygen species may destroy the collagen extracellular matrix scaffolding, thereby inhibiting the migration of new tissue into the wound. Additionally, newly grown cells and healthy tissue may be damaged and killed by the reactive oxygen species fired into the wound site.

Accordingly, the excessive release of indiscriminately destructive reactive oxygen species from a prolonged inflammation phase can inhibit wound healing. The destructive power of reactive oxygen species, however, is necessary for neutrophils and macrophages to clear the wound of debris and infectious organisms and otherwise make the wound repair ready. Inflammation, therefore, is necessary for proper wound healing. The inflammation phase does, however, need to be limited before its detrimental collateral damage begins to outweigh its positive benefits. Accordingly, when a wound has become stalled in, or falls back into, the inflammation phase it is necessary to assist wound healing in transitioning from the inflammation phase to the proliferation phase.

SUMMARY OF THE INVENTION

A polyfunctional radical scavenger hydrogel formulation generally comprising a hydrogel polymer, a first radical scavenger and a second radical scavenger, wherein the first radical scavenger and the second radical scavenger differ with respect to at least one property, may provide extended protection of the wound site and thus assist wounded tissue in transitioning from the inflammation phase to proliferation phase of wound healing.

A wound site is divided into two general areas. The first area is the extracellular space. Across lipid cellular membranes within the wound site is the second area, the intracellular space. Reactive oxygen species are generally produced within the intracellular space and released into the extracellular space. Once released into the extracellular space, reactive oxygen species may prolong the inflammation phase of wound healing through several mechanisms.

For instance, reactive oxygen species released into the extracellular space may attract macrophages to the wound site that could release additional reactive oxygen species, thereby increasing the amount of reactive oxygen species within the wound site. Released reactive oxygen species may also damage and degrade the extracellular matrix thereby depriving wounds of the necessary scaffolding upon which to rebuild and heal. Lipid membranes may also be damaged by reactive oxygen species, thereby compromising cells and/or triggering apoptosis (programmed cell death).

Radical scavengers are capable of protecting a wound site from the damaging effects of reactive oxygen species by removing reactive oxygen species such as, but not limited to, superoxide radicals and/or hydroxyl radicals and other free radicals. Additionally damaging cascades initiated by reactive oxygen species may also be lessened and/or arrested by radical scavengers. To elicit such protection, radical scavengers must have sustained access to the region of the wound site adversely affected by released reactive oxygen species.

Though comprising two general areas, the extracellular and intracellular space, a wound site is a complex environment containing a mixture of regions not equally accessible to all types of molecules. The ability of a radical scavenger to access the various regions within a wound site is dependent upon its properties, such as solubility and molecular weight (i.e. size) to name a few. The inability of a large radical scavenger to readily cross lipid membranes separating the intracellular and extracellular space, for example, may limit its access to the intracellular space. Smaller radical scavengers, however, may more readily cross lipid membranes and thus have the ability to access the intracellular space and the extracellular space. The solubility of a radical scavenger may also influence its ability to access the various regions of the wound site adversely affected by reactive oxygen species. For instance, a hydrophilic radical scavenger (i.e. soluble in water) may have limited access to lipid membranes and/or the internal regions of proteins adversely affected by reactive oxygen species. Even if a radical scavenger can access a region adversely affected by reactive oxygen species, its ability to provide protection may be limited by its rate of diffusion or movement. A radical scavenger having a high rate of diffusion may not remain within an adversely effected region a sufficient amount of time to provide adequate protection. Accordingly, a polyfunctional radical scavenger hydrogel formulation comprising a first radical scavenger and a second radical scavenger, wherein the first radical scavenger and the second radical scavenger differ with respect to at least one property, may assist a wound in transitioning from the inflammation phase by providing extended protection to various regions within the wound site.

The first radical scavenger and the second radical scavenger may differ in various properties such as, but not limited to, solubility, reactivity with various reactive oxygen species, affinity for various reactive oxygen species, stability and molecular weight. The properties possessed by the first radical scavenger and the second radical scavenger control and limit their therapeutic efficacy and duration of action within different regions of the wound site. The properties of the first radical scavenger may also influence the therapeutic efficacy and duration of action of the second radical scavenger within various regions of the wound site adversely affected by reactive oxygen species. Accordingly, a preferred polyfunctional radical scavenger hydrogel formulation comprises a first radical scavenger having a certain set of properties and a second radical scavenger having a second set properties including at least one property that differs from that of the first radical scavenger, as to provide extended protection to various regions of the wound site adversely affected by reactive oxygen species.

The molecular weight of a radical scavenger may influence the ability and/or rate at which the radical scavenger exits and enters a region within the wound site adversely affected by reactive oxygen species. Radical scavengers having a small molecular weight, for instance, may more readily diffuse away from adversely affected regions within the wound site and/or cross cellular membranes. However, if the first radical scavenger and the second radical scavenger readily exited adversely affected regions by diffusing away and/or crossing membranes, then the region would be increasingly unprotected from reactive oxygen species as more of the radical scavengers exited the region. Accordingly, in some embodiments the polyfunctional radical scavenger hydrogel formulation may provide extended protection by including a first radical scavenger having a smaller molecular weight than a second radical scavenger. The molecular weight of at least one of the radical scavengers in some embodiments may be sufficiently large as to severely lessen diffusion of the radical scavenger.

Though generally aqueous, a wound site contains non-aqueous regions such as cellular membranes. As such, extended protection of the wound site may be provided in some embodiments of the polyfunctional radical scavenger hydrogel formulation with radical scavengers capable of accessing the aqueous and non-aqueous regions of the extracellular space. Accordingly, in some embodiments, the first radical scavenger may be more lipid soluble than the second radical scavenger.

Nitrones having a lipid soluble aromatic moiety, for example, may be sufficiently lipid soluble to have access to non-aqueous regions of the wound site adversely affected by reactive oxygen species, such as lipid membranes. Reactive oxygen species can adversely affect cellular membranes by oxidizing lipids. Cellular membranes are walls utilized by cells to protect themselves from their surroundings and to hold themselves together. The basic building blocks of the cellular membranes are lipids. Oxidation of the lipid building blocks of the cellular membrane can create holes within the membrane permitting further cellular damage. Additionally, oxidized lipids can decompose into lipid acyls, detergents which dissolve the cellular membrane. Accordingly, indiscriminate damage by reactive oxygen species to the lipid building blocks of a cellular membrane can destroy the cellular membrane.

The indiscriminate damage of cellular membranes can be amplified by the damaged lipids themselves. The oxidation of a lipid within a cellular membrane by a reactive oxygen species produces a lipid radical within the membrane. Lipid radicals within the cellular membrane can then be further oxidized by oxygen and transformed into a lipid peroxyl radical. The resulting lipid peroxyl can then attack another lipid within the membrane, resulting in an additional lipid peroxyl radical which can then attack another lipid. Each of these peroxyl radicals can decompose into a lipid acyl detergent capable of dissolving the cellular membrane. Accordingly, a single reactive oxygen species indiscriminately damaging a lipid can lead to a cascade of damage causing a catastrophic failure of the cellular membrane of a healthy cell.

A cascade of lipid damage may be lessened and/or arrested by nitrones. Accordingly, nitrones having an aromatic moiety making the nitrone sufficiently lipid soluble to be able to enter a cellular membrane represents one potentially preferred class of radical scavengers. As to inhibit transfer of the nitrone across the membrane, and thereby extend protection of the wound site, it is preferable that the aromatic moiety of the nitrone is not readily susceptible to passive, active and/or facilitated membrane transport (herein after simply referred to as cellular uptake) across at least one cellular membrane within the wound site. Accordingly, nitrones having an aromatic moiety not readily susceptible to cellular uptake across at least one cellular membrane within the wound site represent one potentially preferred class of radical scavengers. In some embodiments of the polyfunctional radical scavenging hydrogel formulation, a first radical scavenger comprising a nitrone having a lipid soluble aromatic moiety not readily susceptible to cellular uptake may be incorporated with a second radical scavenger susceptible to cellular uptake.

Reactive oxygen species present within the wound site may be diverse, including more than one reactive oxygen species. Extended protection within the wound site, therefore, may be provided with a first radical scavenger which more readily removes at least one of the reactive oxygen species present within the wound site than the second radical scavenger. Accordingly, in some embodiments, the first radical scavenger may more readily react with a given reactive oxygen species than the second radical scavenger.

Hydroxylamines are particularly reactive towards reactive oxygen species and thus represent one potentially preferred class of compounds for radical scavengers to be included within the polyfunctional radical scavenger hydrogel formulation. Hydroxylamines remove reactive oxygen species by first being oxidized by a reactive oxygen species to a nitroxide (NO.).

Hydroxylamines may provide extended protection of the extracellular space of the wound site by intercepting and neutralizing reactive oxygen species within the aqueous regions of the wound site that would indiscriminately damage healthy tissue and/or attract macrophages to the wound site. Various hydroxylamines, and their corresponding nitroxide derivatives, however, may be too polar (i.e. not sufficiently lipid soluble) to access and protect some regions within the wound site adversely affected by reactive oxygen species, such as the non-aqueous interior of lipid membranes and/or proteins. Accordingly, while hydroxylamines can intercept and neutralize reactive oxygen species that would indiscriminately damage healthy tissue, a given hydroxylamine may not be able to provide protection to all regions of the wound site adversely affected by reactive oxygen species. In some embodiments of the polyfunctional radical scavenger hydrogel formulation, therefore, the protection provided may be extended by incorporating into the hydrogel formulation a water soluble hydroxylamine and a lipid soluble radical scavenger.

In some embodiments, protection against the adverse effects of reactive oxygen species within the wound site may be extended, at least partially, due to a first radical scavenger which is more reactive towards at least one reactive oxygen species than a second radical scavenger kinetically protecting the second radical scavenger from degradation by a reactive oxygen species. Various hydroxylamines are particularly reactive towards reactive oxygen species and thus hydroxylamines represent one potentially preferred class of compounds for a first radical scavenger that may kinetically protect a second radical scavenger, such as nitrones.

In the presence of reactive oxygen species a nitrone may be transformed into a nitroxide (NO.) capable of scavenging radicals. According to one potential mechanism, the nitroxide formed from the nitrone can be degraded by a hydrolysis reaction to a hydroxylamine. Accordingly, nitrones may be transformed into nitroxides and then degraded into hydroxylamines by reactive oxygen species. It is also possible that nitrones within the wound site may be transformed into a hydroxylamine by a hydrolysis reaction when not in the nitroxide state. As hydroxylamines readily react with reactive oxygen species, when a hydroxylamine and a nitrone are incorporated into a polyfunctional radical scavenger hydrogel formulation the probability of reactive oxygen species reacting with the nitrone may be decreased such that the hydroxylamine kinetically protects the nitrone from degradation. Nitrones thus represent one class of radical scavengers that may be kinetically protected by hydroxylamines.

It is possible that the kinetic protection provided by a hydroxylamine, acting as a first radical scavenger, to a nitrone, acting as a second radical scavenger, may delay degradation following transformation of the nitrone into a nitroxide, thereby potentially extending the protection of the wound site in some embodiments of the polyfunctional radical scavenger hydrogel formulation.

Degradation into a hydroxylamine of a nitrone acting as a second radical scavenger does not completely eliminate the ability of the nitrone to scavenge radicals. As previously discussed, hydroxylamines scavenge reactive oxygen species. Accordingly, the degradation of nitrones acting as a second radical scavenger, into hydroxylamines may extend protection of the wound site by forming a third radical scavenger capable of removing reactive oxygen species that would indiscriminately damage and/or attract macrophages to the wound site.

The radical scavengers may be incorporated into the polyfunctional radical scavenger hydrogel formulation in a variety of manners. Accordingly, in some embodiments all or a portion of the radical scavengers incorporated into the hydrogel formulation may be dissolved and/or suspended in the hydrogel. Having at least a portion of the radical scavengers dissolved and/or suspended in the hydrogel may allow for an initial rapid removal of reactive oxygen species and/or other radicals from the treated wound site.

In some embodiments, all or a portion of the radical scavengers incorporated into the hydrogel formulation may be bonded to a polymer of the hydrogel. Additionally, in some embodiments all or a portion of the radical scavengers incorporated into the hydrogel formulation may be bonded to a molecule that is free of and/or bonded to a polymer of the hydrogel. In some embodiments, bonding the radical scavengers to a polymer of the hydrogel and/or another molecule may provide extended protection within the extracellular space of the wound site by limiting the diffusion of the radical scavengers away from the extracellular space of the wound site and/or cellular uptake into the intracellular space within the wound site. In combination or the alternative, the extended protection may result from radical scavengers bonded to a polymer of the hydrogel and/or another molecule being released over time from the polymer of the hydrogel and/or the other molecule as to replace previously spent radical scavengers.

In some embodiments a first radical scavenger and a second radical scavenger bonded to a polymer of the hydrogel and/or another molecule may remove radicals when so bound. In such embodiments, the spacing should be such that the first radical scavenger does not inhibit and/or interfere with the ability of the second radical scavenger to remove reactive oxygen species. Accordingly, in some embodiments of the polyfunctional radical scavenger hydrogel formulation at least two radical scavengers are bonded to a polymer of the hydrogel and/or another molecule such that the polymer of the hydrogel and/or the other molecule acts as a spacer molecule. When, in such embodiments, the second radical scavenger is intended to provide protection to a region of the wound site different than the first radical scavenger, the spacing should preferably be such that the first radical scavenger does not inhibit or interfere with the ability of the second radical scavenger to access the intended region of the wound site. For instance, when the first radical scavenger and the second radical scavenger differ with respect to lipid and/or water solubility and are intended to scavenge radicals from different areas of the wound site, the spacing should be such that the water soluble nature of the first radical scavenger does not prevent the second radical scavenger from accessing non-aqueous regions of the wound site and the lipid soluble nature of the second radical scavenger does not prevent the ability of the first radical scavenger to access aqueous regions of the wound site.

As previously mentioned, extended protection of the wound site may be provided by pairing a more reactive first radical scavenger with a second radical scavenger such that the first radical scavenger kinetically protects the second radical scavenger from degradation. Such kinetic protection may be achieved when all or a portion of the first radical scavenger incorporated into the hydrogel formulation and/or second radical scavenger incorporated into the hydrogel formulation are bonded to a polymer of the hydrogel and/or another molecule. When such a pairing of a first radical scavenger and a second radical scavenger are bonded to a polymer of the hydrogel and/or another molecule, it is preferred that the first radical scavenger and the second radical scavenger are sufficiently close such that the first radical scavenger can protect the second radical scavenger from being degraded by at least one reactive oxygen species within the wound site.

In some embodiments the protection of the extracellular space of the wound site may be extended by bonding a first radical scavenger and a second radical scavenger to a polymer of the hydrogel and/or another molecule such that the first radical scavenger and the second radical scavenger have zones of influence that are partially overlapping so as to be partially distinct. In such embodiments, the partially distinct nature of the zone of influence of the second radical scavenger may provide the second radical scavenger with an area within its zone of influence relatively unaffected by the presence of the first radical scavenger. This may facilitate the second radical scavenger accessing regions within the wound site not readily accessible to the first radical scavenger. At the same time, the portion of the second radical scavenger's zone of influence affected by the first radical scavenger may permit the first radical scavenger to kinetically protect the second radical scavenger from being degraded by at least one reactive oxygen species within the wound site.

Scavenging nitroxides derived from nitrones may, be on potential mechanism, be degraded by hydrolysis into hydroxylamines. In combination or the alternative, nitrones may be directly degraded via hydrolysis into hydroxylamines. As hydroxylamines are relatively incapable of scavenging lipid radicals within cellular membranes, the degradation of the nitroxide and/or nitrone to a hydroxylamine prevents the nitrone incorporated into the formulation as radical scavenger from providing protection to cellular membranes indiscriminately damaged by reactive oxygen species. However, placing a hydroxylamine near a nitrone may kinetically protect the nitroxide derived from the nitrone from degradation, thereby potentially extending the protection by the nitrone of the non-aqueous regions of the wound site. Accordingly, the protection of non-aqueous regions of the wound site may be extended in some embodiments by bonding a nitrone radical scavenger and a hydroxylamine radical scavenger to a molecule so as to protect the derived nitroxide and/or native nitrone from degradation and thus prolong the protection provided by incorporation of the nitrone into the formulation. In some embodiments this protection may be achieved by placing a hydroxylamine incorporated as a first radical scavenger sufficiently close to a nitrone incorporated as a second radical scavenger to extend the half life of the nitrone.

It is also possible that the partially overlapping zones of influence of a hydroxylamine, as first radical scavenger, and a nitrone, as a second radical scavenger, may extend the protection of the wound site by making the nitrone more efficient at protecting non-aqueous regions of the extracellular matrix. In this scenario, the faster reaction kinetics of the hydroxylamine with various reactive oxygen species may cause the slower reacting nitrone to kinetically favor scavenging lipid radicals.

It is also possible that the fast reaction kinetics of a hydroxylamine acting as a first radical scavenger may extend protection of the wound site by shielding cellular membranes form further damage while a nitrone acting as a second radical scavenger lessens and/or arrests damaging cascades within the lipid membrane.

Spacing the first radical scavenger and the second radical scavenger a sufficient distance as to provide partially overlapping zones of influence can be accomplished by bonding the first radical scavenger to a first end of a spacer molecule and the second radical scavenger to the second end of the spacer molecule. In combination or the alternative, spacing the first radical scavenger and the second radical scavenger as to provide partially overlapping zones of influence can be accomplished by bonding the first radical scavenger and the second radical scavenger to a polymer of the hydrogel. In some embodiments, the derivative scavenging site of the first radical scavenger and the derivative scavenging site of the second radical scavenger may be separated by at least four bonds. The bonds separating the derivative scavenging site of the first radical scavenger and the derivative scavenging site of the second radical scavenger may be any combination of single, resonant, double or triple bonds. The derivative scavenging site of a radical scavenger is the portion of the radical scavenger forming a derivative that scavenges radicals. Accordingly, in the case of a hydroxylamine, a derivative scavenging site is the NOH functional group, which forms nitroxide (NO.). In the case of a nitrone, a derivative scavenging site is the NO⁻ portion of the C=NO⁻ functional group, which forms nitroxide (NO.).

In some embodiments, a molecule comprising a first radical scavenger and a second radical scavenger bonded to different ends of a spacer molecule may be carried upon a polymer of the hydrogel. Such a molecule may be pendant to the polymer of the hydrogel. In combination or the alternative, the molecule may be incorporated into a polymer of the hydrogel as a monomer.

The above potential beneficial effects may be wholly or partially induced by spacing a first radical scavenger a sufficient distance from a second radical scavenger such that the first scavenger influences the reaction kinetics of the second scavenger and provides the first radical scavenger and the second radical scavenger with partially overlapping zones of influence.

While the above potential beneficial effects have been explained with reference to hydroxylamines and nitrones, this has been done merely for purposes of illustration. Other radical scavengers may be substituted for hydroxylamines and/or nitrones to provide all or a portion of the above described benefits, provided the radical scavengers chosen provide a similar pairing of comparative properties necessary to induce the potential beneficial effect desired.

Radical scavengers may be incorporated into the polyfunctional radical scavenger hydrogel formulation in virtually any amount. In some embodiments, the polyfunctional radical scavenger hydrogel may comprise 10% by mass of radical scavengers. The percent by mass of the first radical scavenger may be equal to, less than or greater than that of the second radical scavenger.

The hydrogel of the polyfunctional radical scavenger hydrogel formulation provides the wound to be treated with the positive benefits of a hydrogel wound dressing. For instance, the presence of the hydrogel may absorb exudates, inhibit the formation of the biofilm, maintain the wound in a moistened state and/or provide a matrix for other potentially beneficial therapeutic agents. Therapeutic agents that may be suspended in the hydrogel matrix include atomic silver and silver salts. In some embodiments a quaternary ammonium salt such as benzalkonium chloride or cetylpyridinum chloride may be incorporated as an antibiotic.

The hydrogel may also be utilized to provide an extracellular matrix for the migration and support of new cells. When the hydrogel is to be so used, the hydrogel polymers may wholly or partially comprise collagen. Hydrogel polymers partially comprising collagen may include collagen as a block polymer or copolymer. In combination or the alternative, hydrogel polymers partially comprising collagen may include collagen pendant groups.

In addition to facilitating the hydrogel providing an extracellular matrix, the inclusion of collagen within the hydrogel may facilitate association with the existing extracellular matrix and/or tissues within the wound site. In embodiments in which at least one radical scavenger is carried on a polymer of the hydrogel, this may result in the radical scavenger carried on the hydrogel being in closer proximity to the tissues of the wound, as to extend protection of the wound site by providing better protection against indiscriminate damage by reactive oxygen species. The proximity of a radical scavenger may also be improved by carrying a radical scavenger on a collagen molecule.

Embodiments of the polyfunctional radical scavenger hydrogel formulation may be formulated for use as wound ointments. In combination or the alternative, embodiments of the polyfunctional radical scavenger hydrogel formulation may be formulated for use in wound dressings.

As wounds may also occur during catheterization and the introduction of other medical devices into the body, embodiments of the polyfunctional radical scavenging hydrogel formulation may be formulated to be used as coatings on catheters or other medical or dental devices, including stents, artificial valves, organs and organ parts, pulmonary filters and atrial appendage occlusions devices. The polyfunctional radical scavenging hydrogel formulations may also be used for administration directly to tissues during surgical procedures where wounds are incurred and/or repaired such as bone or tooth fractures, dental root canal procedures and visceral soft tissue repairs where indwelling reservoirs of polyfunctional radical scavenging hydrogel formulations may be used to inhibit the development of excessive inflammation and oxidative stress, such as may occur during tissue repairs, transplantations and implantations.

It should be appreciated that the foregoing and subsequent references to first and second radical scavenger is not to imply or suggest that a polyfunctional radical scavenger hydrogel formulation is limited to including only two radical scavengers. A polyfunctional hydrogel formulation may include any number of radical scavengers. It is preferred, however, that at least two of the radical scavengers differ with respect to at least one property.

DETAILED DESCRIPTION OF THE INVENTION

The polyfunctional radical scavenger hydrogel formulation generally comprises a hydrogel polymer, a first radical scavenger and a second radical scavenger. At least a portion of the first radical scavenger and/or the second radical scavenger may be dissolved, suspended and/or otherwise incorporated into the hydrogel formulation without being bonded to and/or carried on a polymer of the hydrogel. In some embodiments, at least a portion of the first radical scavenger incorporated into the hydrogel formulation and/or the second radical scavenger incorporated into the hydrogel formulation may be bonded to the hydrogel polymer and/or to a molecule other than a polymer of the hydrogel. In some embodiments the hydrogel polymer and/or another molecule to which a portion of the first radical scavenger incorporated into the hydrogel formulation and a portion of the second radical scavenger incorporated into the hydrogel formulation are bonded may act as a spacer molecule.

In embodiments in which a first radical scavenger and a second radical scavenger are bonded to a spacer molecule, the first radical scavenger and the second radical scavenger may be sufficiently spaced such that the hydrophilic nature of the first radical scavenger does not prevent the second radical scavenger from accessing non-aqueous regions of the wound site and the lipid soluble nature of the second radical scavenger does not prevent the first radical scavenger from accessing aqueous regions of the wound site. In combination or the alternative, the first radical scavenger and the second radical scavenger may be sufficiently spaced such that the first radical scavenger kinetically protects the second radical scavenger. In some embodiments in which a first radical scavenger and a second radical scavenger are bonded to a spacer molecule, the first radical scavenger and the second radical scavenger may be separated a sufficient distance as to provide the first radical scavenger with a zone of influence partially overlapping the zone of influence of the second radical scavenger.

The first radical scavenger may be any radical scavenger capable of scavenging reactive oxygen species. Preferably the first radical scavenger comprises a sterically hindered amine. An amine can be sterically hindered by incorporation of a tertiary carbon adjacent to the nitrogen of the amine. The sterically hindered amine may be a primary amine, a secondary amine, a tertiary amine and/or a cyclic amine.

Primary and secondary sterically hindered amines that may be utilized in the polyfunctional radical scavenger hydrogel formulation can be N-tert-butylamine derivatives in accordance with general formula 1.

Formula 1

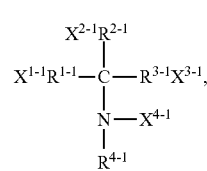

where $R^{1-1}$, $R^{2-1}$ and $R^{3-1}$ are each a carbon chain having a length of C1 to C12, where $X^{1-1}X^{2-1}$ and $X^{3-1}$ are each selected from H, OH, acrylate, methacrylate, N-(alkyl carboxyl)-acrylamide, and N-(alkyl carboxyl)-methacrylamide, where $X^{4-1}$ is selected from H, OH, O and O., and where $R^{4-1}$ is selected from H and a carbon chain having a length of C1 to C12.

Carbon chains at $R^{1-1}$, $R^{2-1}$, $R^{3-1}$ and $R^{4-1}$ may comprise linear, branched and/or cyclic portions. Cyclic portions of the carbon chains at $R^{1-1}$, $R^{2-1}$, $R^{3-1}$ and $R^{4-1}$ may be aromatic. In some embodiments any of the carbon chains at $R^{1-1}$, $R^{2-1}$, $R^{3-1}$, and $R^{4-1}$ may be substituted. Embodiments are also possible in which a carbon of any of the carbon chains $R^{1-1}$, $R^{2-1}$, $R^{3-1}$ and $R^{4-1}$ is replaced with another atom as to create a heterogeneous chain.

For example, the carbon chain at $R^{3-1}$ could be a methyl phenyl and $X^{3-1}$ could be H as to provide a first radical scavenger comprising a sterically hindered amine in accordance with general formula 1.1

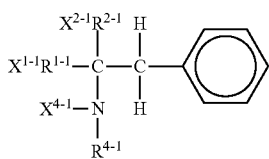

Formula 1.1 where $R^{1-1}$ and $R^{2-1}$ are each a carbon chain having a length of C1 to C12, where $X^{1-1}$ and $X^{2-1}$ are each selected from H, OH, acrylate, methacrylate, N-(alkyl carboxyl)-acrylamide, and N-(alkyl carboxyl)-methacrylamide, where $X^{4-1}$ is selected from H, OH, O and O., and where $R^{4-1}$ is selected from H and a carbon chain having a length of C1 to C12.

In some embodiments the phenyl ring of general formula 1.1 may be substituted as to increase lipid solubility or water solubility. Embodiments are also possible in which the phenyl ring of general formulation 1.1 is substituted to inhibit or potentiate cellular uptake across at least one membrane within the wound site. In some embodiments, a carbon of the phenyl ring of general formula 1.1 may be replaced with another atom as to create a heterogeneous aromatic ring. The phenyl ring of general formula 1.1 maybe fused and/or conjugated with another aromatic ring in some embodiments.

Cyclic sterically hindered hydroxylamines that may be utilized in the polyfunctional radical scavenger hydrogel formulation can be derived from pyrrole derivatives in accordance with general formula 2.

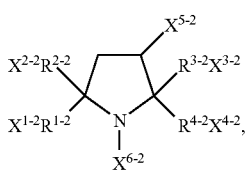

Formula 2 where $R^{1-2}$, $R^{2-2}$, $R^{3-2}$ and $R^{4-2}$ are each a carbon chain having a length of C1 to C12, where $X^{1-2}$, $X^{2-2}$, $X^{3-2}$, $X^{4-2}$ and $X^{5-2}$ are each selected from H, OH, acrylate, methacrylate, N-(alkyl carboxyl)-acrylamide, and N-(alkyl carboxyl)-methacrylamide, and where $X^{6-2}$ is selected from H, OH, O and O.

Carbon chains at $R^{1-2}$, $R^{2-2}$, $R^{3-2}$ and $R^{4-2}$ may comprise linear, branched and/or cyclic portions. Cyclic portions of the carbon chains at $R^{1-2}$, $R^{2-2}$, $R^{3-2}$ and $R^{4-2}$ may be aromatic. In some embodiments any of the carbon chains at $R^{1-2}$, $R^{2-2}$, $R^{3-2}$ and $R^{4-2}$ may be substituted. Embodiments are also possible in which a carbon of any of the carbon chains $R^{1-2}$, $R^{2-2}$, $R^{3-2}$ and $R^{4-2}$ is replaced with another atom as to create a heterogeneous chain.

Cyclic sterically hindered hydroxylamines that may be utilized in the polyfunctional radical scavenger hydrogel formulation can also be derived from piperidine derivatives in accordance with general formula 3.

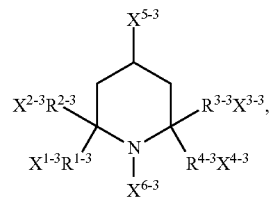

Formula 3 where $R^{1-3}$, $R^{2-3}$, $R^{3-3}$ and $R^{4-3}$ are each a carbon chain having a length of C1 to C12, where $X^{1-3}$, $X^{2-3}$, $X^{3-3}$, $X^{4-3}$ and $X^{5-3}$ are each selected from H, OH, acrylate, methacrylate, N-(alkyl carboxyl)-acrylamide, and N-(alkyl carboxyl)-methacrylamide, and where $X^{6-3}$ is selected from H, OH, O and O..

Carbon chains at $R^{1-3}$, $R^{2-3}$, $R^{3-3}$ and $R^{4-3}$ may comprise linear, branched and/or cyclic portions. Cyclic portions of the carbon chains at $R^{1-3}$, $R^{2-3}$, $R^{3-3}$ and $R^{4-3}$ may be aromatic. In some embodiments any of the carbon chains at $R^{1-3}$, $R^{2-3}$, $R^{3-3}$ and $R^{4-3}$ may be substituted. Embodiments are also possible in which a carbon of any of the carbon chains $R^{1-3}$, $R^{2-3}$, $R^{3-3}$ and $R^{4-3}$ is replaced with another atom as to create a heterogeneous chain.

When any of $X^{1-1}$, $X^{2-1}$ and $X^{3-1}$ in general formula 1, or any of $X^{1-2}$, $X^{2-2}$, $X^{3-2}$, $X^{4-2}$ and $X^{5-2}$ in general formula 2, or any $X^{1-3}$, $X^{2-3}$, $X^{3-3}$, $X^{4-3}$ and $X^{5-3}$ in general formula 3, are any of the functional groups OH, acrylate, methacrylate, N-(alkyl carboxyl)-acrylamide, and N-(alkyl carboxyl)-methacrylamide, the radical scavenger may be joined to the hydrogel polymer and/or another molecule by $X^{1-1}$, $X^{2-1}$ or $X^{3-1}$, in the case of general formula 1, or $X^{1-2}$, $X^{2-2}$, $X^{3-2}$, $X^{4-2}$ or $X^{5-2}$ in the case of general formula 2, or $X^{1-3}$, $X^{2-3}$, $X^{3-3}$, $X^{4-3}$ or $X^{5-3}$ in the case of general formula 3. When so joined to the hydrogel polymer, the radical scavenger may be pendant to the hydrogel polymer and/or a monomer of the hydrogel polymer.

The second radical scavenger may be any radical scavenger capable of scavenging reactive oxygen species. The second radical scavenger may be chosen so as to provide a radical scavenger with properties different than that of the first radical scavenger. For example, the second radical scavenger may have different reaction kinetics with regards to at least one reactive oxygen species than the first radical scavenger. In combination or the alternative, the second radical scavenger may be more lipid soluble than the first radical scavenger.

The second radical scavenger may also be chosen so as to have radical scavenging capabilities not possessed by the first radical scavenger. For instance, the second radical scavenger may be more capable of scavenging lipid radicals than the chosen first radical scavenger.

The second radical scavenger may be capable of being degraded into a third radical scavenger.

Though not necessary, it is preferred that the second radical scavenger meet at least a portion of the above identified criteria. Accordingly a preferred second radical scavenger is a sterically hindered nitrone. Sterically hindered nitrones that may be utilized in the polyfunctional radical scavenger hydrogel formulation can be derived from aryl N-tert-butylnitrone derivatives in accordance with the general formula 4.

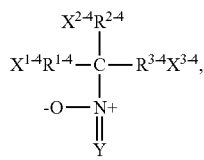

Formula 4 where $R^{1-4}$, $R^{2-4}$, and $R^{3-4}$ are each a carbon chain having a length of C1 to C12,
where $X^{1-4}$, $X^{2-4}$, and $X^{3-4}$ are each selected from H, OH, acrylate, methacrylate, N-(alkyl carboxyl)-acrylamide, and N-(alkyl carboxyl)-methacrylamide, and
where Y is an aromatic moiety comprising an aromatic ring having a substituent containing a carbon that is bonded to the nitrogen by the double bond.

In some embodiments, the aromatic moiety Y in general formula 4 may be represented by the general formula:

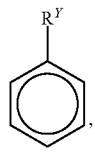

where $R^Y$ is a substituent having a carbon that is bonded to the nitrogen of general Formula 4 by the double bond.

Carbon chains at $R^{1-4}$, $R^{2-4}$ and $R^{3-4}$ may comprise linear, branched and/or cyclic portions. Cyclic portions of the carbon chains at $R^{1-4}$, $R^{2-4}$ and $R^{3-4}$ may be aromatic. In some embodiments any of the carbon chains at $R^{1-4}$, $R^{2-4}$ and $R^{3-4}$ may be substituted. Embodiments are also possible in which a carbon of any of the carbon chains $R^{1-4}$, $R^{2-4}$ and $R^{3-4}$ is replaced with another atom as to create a heterogeneous chain.

In some embodiments the aromatic moiety Y of general formula 4 may comprise one or more substituents increasing lipid solubility and/or limiting cellular uptake across at least one cellular member within the wound site. For example the aromatic moiety Y of general formula 4 may comprise a halide containing substituent. In combination of the alternative, a carbon of the aromatic moiety Y may be replaced with another atom as to create a heterocyclic aromatic moiety. In some embodiments, the aromatic ring of the aromatic moiety Y may be fused and/or conjugated with another aromatic ring. Preferably, the polyfunctional radical scavenger hydrogel formulation may comprise derivatives of formula 4 in which the aromatic moiety Y is lipid soluble and not subject to cellular uptake across at least one cellular membrane within the wound site via active and/or facilitated transport. Accordingly, the aromatic moiety Y may be a methyl phenyl as to produce a molecule in accordance with general formula 4.1.

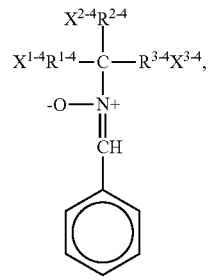

Formula 4.1 where $R^{1-4}$, $R^{2-4}$, and $R^{3-4}$ are each a carbon chain having a length of C1 to C12, and
where $X^{1-4}$, $X^{2-4}$, and $X^{3-4}$ are each selected from H, OH, acrylate, methacrylate, N-(alkyl carboxyl)-acrylamide, and N-(alkyl carboxyl)-methacrylamide.

The lipid solubility of a molecule in accordance with general formula 4.1 may also be increased by utilizing a phenyl or another aromatic moiety for any of $R^{1-4}$, $R^{2-4}$ and $R^{3-4}$. For instance, selecting as $R^{3-4}$ a methyl phenyl and selecting as $X^{3-4}$H, as to provide a molecule in accordance with general formula 4.2, may provide a radical scavenger having improved access to a lipid membrane and/or duration action within a lipid membrane.

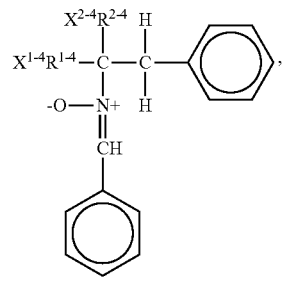

Formula 4.2 where $R^{1-4}$ and $R^{2-4}$ are each a carbon chain having a length of C1 to C12, and
where $X^{1-4}$, $X^{2-4}$, and $X^{3-4}$ are each selected from H, OH, acrylate, methacrylate, N-(alkyl carboxyl)-acrylamide, and N-(alkyl carboxyl)-methacrylamide.

When any of $X^{1-4}$, $X^{2-4}$ and $X^{3-4}$ in general formula 4 are any of the functional groups OH, acrylate, methacrylate, N-(alkyl carboxyl)-acrylamide, and N-(alkyl carboxyl)-methacrylamide, the radical scavenger may be joined to the hydrogel polymer and/or another molecule by $X^{1-4}$, $X^{2-4}$ or $X^{3-4}$. When so joined to the hydrogel polymer, the radical scavenger may be pendant to the hydrogel polymer and/or a monomer of the hydrogel polymer.

In some embodiments, at least a portion of the first radical scavenger incorporated into the hydrogel formulation and a portion of the second radical scavenger incorporated into the hydrogel formulation are bonded to a spacer molecule. Preferably the spacer molecule separates the first radical scavenger from the second radical scavenger a sufficient distance so as to provide the first radical scavenger with a zone of influence partially overlapping the zone of influence of the second radical scavenger. Spacing the first radical scavenger and the second radical scavenger a sufficient distance as to provide partially overlapping zones of influence can be accomplished by bonding the first radical scavenger to a first end of a molecule and the second radical scavenger to the second end of the molecule. Preferably, the derivative scavenging site of the first radical scavenger and the derivative scavenging site of the second radical scavenger are separated by at least four bonds. The bonds separating the derivative scavenging site of the first radical scavenger and the derivative scavenging site of the second radical scavenger may be any combination of single, resonant, double or triple bonds.

In some embodiments the spacer molecule may be bonded to the hydrogel polymer of the polyfunctional radical scavenger hydrogel formulation. In such embodiments, the first radical scavenger and/or second radical scavenger may be a monomer of the hydrogel polymer, a monomer of a block polymer of the hydrogel polymer, and/or a monomer of a copolymer of the hydrogel polymer. In such a situation the hydrogel polymer may be synthesized such that a monomer comprising the first radical scavenger is spaced a sufficient distance along the hydrogel polymer from a monomer comprising the second radical scavenger. In combination or the alternative, the first radical scavenger and/or second radical scavenger may be pendent to the hydrogel polymer.

In addition to the sterically hindered nitrones and sterically hindered amines corresponding to general formulae 1-4, other radical scavengers may be utilized in synthesizing embodiments of the polyfunctional radical scavenger formulation in which at least a portion of the first radical scavenger and/or second radical scavenger incorporated into the hydrogel formulation are bonded to the polymer of the hydrogel and/or another molecule.

The polyfunctional radical scavenger may be synthesized from polyethylene glycols and/or polypropylene glycols monomers carrying pendant nitrones and/or sterically hindered amines. In combination or the alternative, hydroxyethyl methacrylate and/or hydroxymethyl acryloyl chloride carrying nitrones and/or sterically hinder amines may be utilized to incorporate the first and second radical scavengers into the hydrogel polymer. When carried upon hydroxyethyl methacrylate, the aromatic nitrones, sterically hindered amines and/or other radical scavengers may be incorporated into the polymer by converting the hydroxyethyl methacrylate to glycidic acid.

If a sterically hindered nitrone and/or sterically hindered hydroxylamine are to be utilized as a scavenger in the polyfunctional radical scavenger hydrogel formulation, they can be produced from a synthon in accordance with compound A.

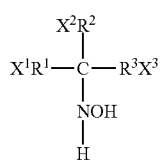

Compound A where $R^1$, $R^2$ and $R^3$ are carbon chains,
where $X^1$, $X^2$ and $X^3$ are selected from H and OH, and at least one of $X^1$, $X^2$ and $X^3$ is OH.

Utilization of compound A, or a derivative thereof, as a synthon in the production nitrone may be accomplished via a condensation reaction. During such a condensation reaction the carbon chain $R^1$, $R^2$ and/or $R^3$ having a hydroxyl may be activated by deprotonation of the hydroxyl or by dehydration of the hydroxyl. The activated carbon chain can then be condensed with a suitable aromatic or heterocyclic aldehyde or ketone to generate the desired nitrone. The aldehyde or ketone condensed with compound A may or may not include phenolic, carboxylic or amino substituents.

Activation of the carbon chain creates an electrophile at the carbon adjacent the hydroxyl. During condensation, this electrophile can be nucleophilically attacked by the carbonyl oxygen of the aldehyde or ketone. At the same time, the electrophile carbonyl carbon of the aldehyde or ketone can be nucleophilically attacked by the nitrogen of the same or different molecule of compound A. If the aldehyde or ketone is attacked by the same molecule of compound A, the combined nucleophilic attacks forms a ring intermediate. Deportation of the attacking nitrogen creates a double bond between the nitrogen and carbonyl carbon of the aldehyde or ketone. At the same time, protonation of the carbonyl oxygen provides the activated carbon chain with a hydroxyl formed from the carbonyl oxygen, thereby forming an alcohol or a carboxylic acid. The amino, carboxyl, phenolic and/or alcoholic hydroxyl groups that can be provided by the condensation of compound A with an aldehyde or ketone provide facile routes to the desired esters, carbamates and amides.

Condensation reactions utilizing compound A, or a derivative thereof, to produce a nitrone may be accomplished via base catalyzed condensation in a one pot synthetic procedure.

In the case of a C-nitro compound corresponding to the hydroxylamine to be used, synthons in accordance with compound A can be generated in situ by reduction with zinc dust and acetic acid or ammonium chloride.

At least a portion of the first radical scavenger and/or the second radical scavenger incorporated into the hydrogel formulation may be bonded to a wide variety of molecules, which in some embodiments may serve as a spacer molecule.

In some embodiments, at least a portion of the first radical scavenger and/or second radical scavenger incorporated into the hydrogel formulation may be bonded to a portion of the hydrogel polymer.

In some embodiments at least a portion of the first radical scavenger and/or second radical scavenger incorporated into the hydrogel formulation may be bonded to a distinct molecule separating the derivative scavenging site of the first radical scavenger from the derivative scavenging site the second radical scavenger.

In some embodiments at least a portion of the first radical scavenger incorporated into the hydrogel formulation and a portion of the second radical scavenger incorporated into the hydrogel formulation are bonded to a molecule such that the zone of influence of the first radical scavenger partially overlaps with the zone of influence of the second radical scavenger.

A spacer molecule distinct from the hydrogel polymer may be formed by $R^{3-1}X^{3-1}$ of general formula 1 reacting with $R^{2-4}X^{2-4}$ of general formula 4. Preferred molecules among the various molecules that may be produced from a such reaction include molecules according to general formula 5.

$$-CH_2X^{1-5}(CH_2)_nX^{2-5}CH_2-,\qquad \text{Formula 5:}$$

where $X^{1-5}$ and $X^{2-5}$ are selected from amide and carboxyl.

Joined first and second radical scavengers formed by the reaction of $R^{3-1}X^{3-1}$ of general formula 1 with $R^{2-4}X^{2-4}$ of general formulae 4 as to incorporate a molecule according to general formula 5 include bifunctional radical scavengers represented by general formula 6.

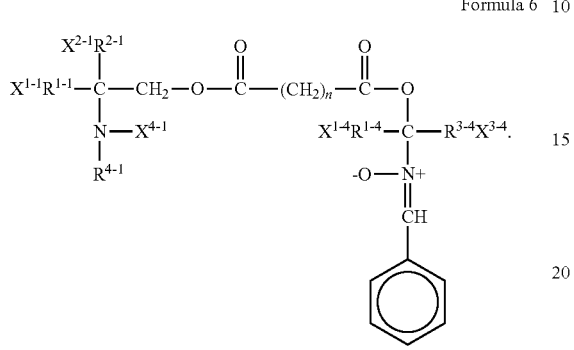

Formula 6

Joined first and second radical scavengers according to general formula 6, and others formed by $R^{3-1}X^{3-1}$ of general formula 1 reacting with $R^{2-4}X^{2-4}$ of general formula 4, may be joined to the hydrogel polymer by $X^{1-1}$ or $X^{2-1}$ of general formula 1 and/or by $X^{1-4}$ or $X^{3-4}$ of general formula 4. Joined first and second radical scavengers according to general formula 6 may also be joined to a monomer of a hydrogel polymer by a carbonyl of the molecule according to general formula 5.

A molecule distinct from the hydrogel polymer may likewise be formed by $X^{5-2}$ of general formula 2 or of $X^{5-3}$ of general formula 3 reacting with $R^{2-4}X^{2-4}$ of general formulae 4. Preferred molecules among the various molecules that may be produced from such a reaction include molecules according to general formula 7.

$$—X^{1-6}(CH_2)_n X^{2-6} CH_2—,$$ Formula 7:

where $X^{1-6}$ and $X^{2-6}$ are selected from amide and carboxyl.

Joined first and second radical scavengers formed by $X^{5-3}$ of general formula 3 reacting with $R^{2-4}X^{2-4}$ of general formulae 4 as to incorporate a molecule according to general formula 7 include bifunctional radical scavengers represented by general formula 8.

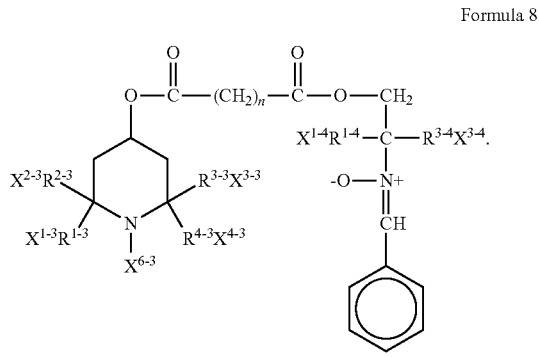

Formula 8

Joined first and second radical scavengers according to general formula 8, and others formed by $X^{5-3}$ of general formula 3 reacting with $R^{2-4}X^{2-4}$ of general formulae 4, may be joined to the hydrogel polymer by $X^{1-3}$, $X^{2-3}$, $X^{3-3}$ or $X^{4-3}$ of general formula 3 and/or by $X^{1-4}$ or $X^{3-4}$ of general formula 4. Joined first and second radical scavengers according to general formula 8 may also be joined to a monomer of the hydrogel polymer by a carbonyl of the molecule according to general formula 7.

Joined first and second radical scavengers formed by $X^{5-3}$ of general formula 3 reacting with $R^{2-4}X^{2-4}$ of general formula 4 as to incorporate a molecule according to general formula 7 also include bifunctional radical scavengers represented by general formula 9.

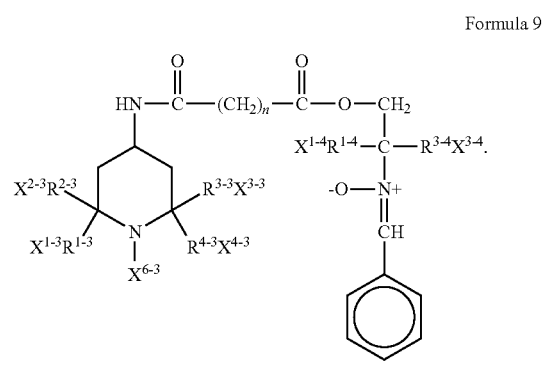

Formula 9

Joined first and second radical scavengers according to general formula 9, and others formed by $X^{5-3}$ of general formula 3 reacting with $R^{2-4}X^{2-4}$ of general formula 4, may be joined to the hydrogel polymer by $X^{1-3}$, $X^{2-3}$, $X^{3-3}$ or $X^{4-3}$ of general formula 3 and/or by $X^{1-4}$ or $X^{3-4}$ of general formula 4. Joined first and second radical scavengers according to general formula 9 may also be joined to a monomer of the hydrogel polymer by a carbonyl of the molecule according to general formula 7.

The hydrogel polymer of the polyfunctional radical scavenger hydrogel formulation is not particular limited. Preferred hydrogel polymers include block and/or copolymers of collagen, PLURONIC® PF127 (triblock ethylene oxide/propylene oxide), 2-hydroxyethyl methacrylate, acrylate, keratin, pectins, polyvinylpyrrolidones and singly.

Polyfunctional radical scavenger hydrogel formulations generally comprising a hydrogel, a first radical scavenger and a second radical scavenger, wherein at least a portion of the first radical scavenger incorporated into the hydrogel formulation and a portion of the second radical scavenger incorporated into the hydrogel formulation are bonded to the hydrogel, can provide sustained radical scavenging activity lasting up to ninety-six hours.

The ability of a polyfunctional radical scavenger hydrogel formulation to offer extended protection of a wound site over a period of time can be assessed in the following manner. Neutrophils may be seeded into a first chamber having a porous surface. After 2 hours, the neutrophils may be rinsed with DPBS to remove neutrophils non-adherent to the chamber. The chamber may then be moved to a second chamber containing the polyfunctional radical scavenger hydrogel formulation to be assessed.

In addition to the polyfunctional radical scavenger hydrogel formulation to be assessed, a fluorescent probe for extracellular reactive oxygen species and an fMLP solution, which stimulates neutrophils to produce reactive oxygen species, should be added to the second chamber.

After incubation with the probe and stimulate, the activity of the polyfunctional radical scavenger hydrogel formulation can be observed for a period of time. After which, supernatants from the first chamber may be removed to a separate well plate for fluorescence detection.

As controls, neutrophils should be identically seeded in control chambers. The control chambers may be incubated in a second chamber containing only the probe and stimulant. After incubation with the probe and stimulant for the same period of time as neutrophils exposed to the polyfunctional radical scavenger hydrogel formulation being assessed, supernatants from the control chamber may be removed to a separate well plate for fluorescence detection.

An increase in the fluorescence detected over time will indicate sustained levels of reactive oxygen species. Conversely, a decrease in the fluorescence detected over time indicates sustained scavenging of reactive oxygen species by the polyfunctional radical scavenger hydrogel formulation being assessed.

A polyfunctional radical scavenger hydrogel formulation generally comprising a hydrogel, first radical scavenger and a second radical scavenger, wherein at least a portion of the first radical scavenger incorporated into the hydrogel formulation and a portion of the second radical scavenger incorporated into the hydrogel formulation are bonded to the hydrogel, can provide immediate and sustained radical scavenging activity lasting up to ninety-six hours. The immediate and sustained radical scavenging activity of polyfunctional radical scavenger hydrogel formulation allows such a formulation to be used as coatings on medical devices introduced into the body to suppress inflammation and promote transition into the proliferation phase in wounds generated by the insertion of the device for a prolonged period of time. Accordingly, polyfunctional radical scavenger hydrogel formulation in accordance with the present disclosure are beneficial coatings for catheters, stents, artificial valves, organs or organ parts, pulmonary filters, atrial appendage occlusions devices and other medical or dental devices. The polyfunctional radical scavenging hydrogel formulations may also be used for administration directly to tissues during surgical procedures where wounds are incurred and/or repaired such as bone or tooth fractures, dental root canal procedures and visceral soft tissue repairs where indwelling reservoirs of polyfunctional radical scavenging hydrogel formulations may be used to inhibit the development of excessive inflammation and oxidative stress such as occurs during tissue repairs, transplantations and implantations.

The immediate and sustained radical scavenging activity of bifunctional radical scavengers carried on hydrogel polymers also makes hydrogel compositions in accordance with the present disclosure beneficial for use in wound ointments and wound dressings.

These and other advantages may be realized by polymer compositions in accordance with the present disclosure and detailed in the following claims.

Although the foregoing has been described with reference to potential modes of action and/or mechanisms of action for purposes of illustration and clarity of understanding, it should be appreciated that polyfunctional radical scavenger hydrogel formulations in accordance with the present invention are not limited to the potential modes of action and mechanisms of action discussed herein. Polyfunctional radical scavenger hydrogel formulations within the scope of the invention may utilize modes of action and/or mechanisms of action in combination with or in the alternative to those discussed herein.

We claim:

1. A method of treating a wound comprising the step of: contacting a polyfunctional free radical scavenger hydrogel composition with a wounded tissue; and wherein the polyfunctional free radical scavenger hydrogel composition comprises: a hydrogel; a first free radical scavenger, and a second free radical scavenger and wherein the first free radical scavenger comprises a sterically hindered amine of the general formula:

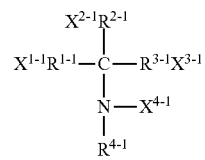

wherein $R^{1-1}$ is a carbon chain having a length of C1 to C12, wherein the carbon chain is linear, branched, cyclic, aromatic portion, or a combination thereof, wherein $R^{2-1}$ is a carbon chain having a length of C1 to C12, wherein the carbon chain is linear, branched, cyclic, aromatic portion, or a combination thereof, wherein $R^{3-1}$ is selected from the group consisting of H and a carbon chain having a length of C1 to C12, wherein the carbon chain is linear, branched, cyclic, aromatic portion, or a combination thereof, wherein $R^{4-1}$ is selected from the group consisting of H and a carbon chain having a length of C1 to C12, wherein the carbon chain is linear, branched, cyclic, aromatic portion, or a combination thereof, wherein $X^{1-1}$ is selected from the group consisting of H, OH, acrylate, and methacrylate, wherein $X^{2-1}$ is selected from the group consisting of H, OH, acrylate, and methacrylate, wherein $X^{3-1}$ is selected from the group consisting of H, OH, acrylate, and wherein $X^{4-1}$ is selected from the group consisting of H, OH, O and O-; and the second free radical scavenger is lipid soluble and wherein the second free radical scavenger is present in an amount to provide protection against reactive oxygen species within the wounded tissue, the second free radical scavenger comprising a sterically hindered nitrone of the general formula:

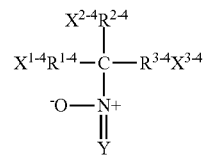

wherein $R^{1-4}$ is a carbon chain having a length of C1 to C12, wherein the carbon chain is linear, branched, cyclic, aromatic portion, or a combination thereof, wherein $R^{2-4}$ is a carbon chain having a length of C1 to C12, wherein the carbon chain is linear, branched, cyclic, aromatic portion, or a combination thereof, wherein $R^{3-4}$ is a carbon chain having a length of C1 to C12, wherein the carbon chain is linear, branched, cyclic, aromatic portion, or a combination thereof, wherein $X^{1-4}$ is selected from the group consisting of H, OH, acrylate, and methacrylate, wherein $X^{2-4}$ is selected from the group consisting of H, OH, acrylate, and methacrylate, wherein $X^{3-4}$ is selected from the group consisting of H, OH, acrylate, and methacrylate, wherein Y is a lipid soluble aromatic moiety comprising an aromatic ring having a substituent containing a carbon that is bonded to the nitrogen by the double bond and the lipid soluble aromatic moiety inhibits transfer of the nitrone across a cellular membrane.

2. The method of claim 1, wherein the first free radical scavenger slows the degradation of the second free radical scavenger.

3. The method of claim 2, wherein the first free radical scavenger and the second free radical scavenger are suspended or dissolved within the hydrogel.

4. The method of claim 1, wherein the wounded tissue includes a wound that has already been incurred prior to being contacted with the polyfunctional free radical scavenger hydrogel composition or a wound that has been surgically repaired.

5. The method of claim 1, wherein the lipid soluble aromatic moiety is not subject to cellular uptake across at least one cellular membrane within the wound.

6. The method of claim 5, wherein the second free radical scavenger has a higher molecular weight than the first free radical scavenger.

7. The method of claim 1, wherein the wounded tissue is a surgical wound and the first free radical scavenger is present in an amount that provides protection of the surgical wound against free radicals.

8. The method of claim 1, wherein the first free radical scavenger and the second free radical scavenger are suspended in the hydrogel.

9. The method of claim 1, wherein the first free radical scavenger and the second free radical scavenger are dissolved in the hydrogel.

10. The method of claim 1, wherein the step of contacting the polyfunctional free radical scavenger hydrogel composition with the wounded tissue provides protection of an extracellular space and assists the wounded tissue in transitioning from an inflammation phase to a proliferation phase of wound healing and wherein the hydrogel is a polymers chosen from the group consisting of: polymers of collagen, triblock ethylene oxide, triblock propylene oxide, 2-hydroxyethyl methacrylate, acrylate, keratin, pectins, polyvinylpyrrolidones.

11. The method of claim 1, wherein polyfunctional free radical scavenger hydrogel composition is a coating on a medical device chosen from the group consisting of: catheters, stents, artificial valves, organs, and organ parts, pulmonary filters and atrial appendage occlusions devices.

12. The method of claim 1, wherein step of contacting a polyfunctional free radical scavenger hydrogel composition with the wounded tissue comprises either applying the polyfunctional free radical scavenger hydrogel composition to tissues during surgical procedures where wounds are incurred or repaired or by contacting the wounded tissue with a medical device or a dental device coated with the polyfunctional free radical scavenger hydrogel composition.

13. The method of claim 1, wherein the polyfunctional free radical scavenger hydrogel composition is in the form of an ointment or a composition applied to a wound dressing.

14. The method of claim 1, wherein the polyfunctional free radical scavenger composition comprises a plurality of polyfunctional free radical scavengers.

15. The method of claim 14, wherein the polyfunctional free radical scavengers consist of the first free radical scavenger and the second free radical scavenger.

16. A method of treating a wounded tissue that occurs as a result of tissue repairs, transplantations or implantations, the method comprising the step of:

applying a hydrogel composition to the wounded tissue; and wherein the hydrogel composition comprises: a hydrogel, a plurality of free radical scavengers comprising a hydroxylamine and a sterically hindered nitrone; and wherein the hydrogel composition is present as either 1) a coating on a surface of a medical device or a dental device or 2) an ointment applied directly application to the wounded tissue.

17. The method of claim 16, wherein the medical device is chosen from the group consisting of a catheter, a stent, and artificial valve, an organ, an organ parts, a pulmonary filter, and an atrial appendage occlusions device.

18. The method of claim 16, wherein the hydrogel composition is in the form of an ointment and the step of applying the hydrogel composition to the wounded tissue comprises applying the hydrogel composition to tissues during surgical procedures and visceral soft tissue repairs.

* * * * *